United States Patent [19]
Gibson et al.

[11] Patent Number: 5,928,609
[45] Date of Patent: Jul. 27, 1999

[54] ODOR SENSOR

[75] Inventors: Timothy David Gibson, Leeds; Peter Puttick, Surrey; John Neal Hulbert; Robert Wilson Marshall, both of Leeds, all of United Kingdom; Zhuoshu Li, Wallington, N.J.

[73] Assignee: Bloodhound Sensors, Ltd., United Kingdom

[21] Appl. No.: 08/793,957

[22] PCT Filed: Sep. 6, 1995

[86] PCT No.: PCT/GB95/02117

§ 371 Date: Jul. 14, 1997

§ 102(e) Date: Jul. 14, 1997

[87] PCT Pub. No.: WO96/07901

PCT Pub. Date: Mar. 14, 1996

[30] Foreign Application Priority Data

Sep. 6, 1994 [GB] United Kingdom ............... 9417913

[51] Int. Cl.[6] .................. G01N 27/407; G01N 33/48
[52] U.S. Cl. ................. 422/90; 422/83; 73/23.34; 73/23.36
[58] Field of Search .................. 422/90, 98, 83; 73/23.2, 23.34, 23.36

[56] References Cited

U.S. PATENT DOCUMENTS

| 4,224,071 | 9/1980 | Buell | 106/22 |
|---|---|---|---|
| 4,415,876 | 11/1983 | Yasuda et al. | 338/34 |
| 4,534,355 | 8/1985 | Potter | 128/635 |
| 4,839,020 | 6/1989 | Yamaguchi et al. | 204/431 |
| 4,887,455 | 12/1989 | Payne et al. | 73/27 R |
| 5,034,192 | 7/1991 | Wrighton et al. | 422/82.07 |
| 5,071,770 | 12/1991 | Kolesar | 436/151 |

FOREIGN PATENT DOCUMENTS

| 86/01599 | 3/1986 | WIPO . |
|---|---|---|
| 93/03355 | 2/1993 | WIPO . |

OTHER PUBLICATIONS

Pearce et al., "Machine Olfactoin: Intelligent Sensing of Odours'", Internation Conference on Systems, Man and Cybernetics. Conference Proceedings, vol. 5, pp. 165–170, Oct. 1993.

EG&G Princeton Applied Research, "Interdigitated Microsensor Electrodes", IME 1550 Series, No Date Supplied.

TC Pierce, et al. "Machine Olfaction: Intelligent Sensing of Odours", 1993, International Conference on Systems, Man and Cybernetics. Conference Proceedings, vol. 5, Oct. 17 1993 Le Touquet, France.

Paolo Pelosi and Krishna Persaud, "Gas Sensors, Towards an Artificial Nose", ASI series vol. F43, Sensors and Sensory Systems For Advanced Robots, Springer Verlag Berlin Hiedelberg, 1988.

Primary Examiner—Lyle A. Alexander
Attorney, Agent, or Firm—Beyer & Weaver, LLP

[57] ABSTRACT

Provided is an odour sensor which may be useful for discriminating between the odour of human or other mammalian individuals, and perimidine monomers and polymers which may be used in such a sensor.

5 Claims, 8 Drawing Sheets

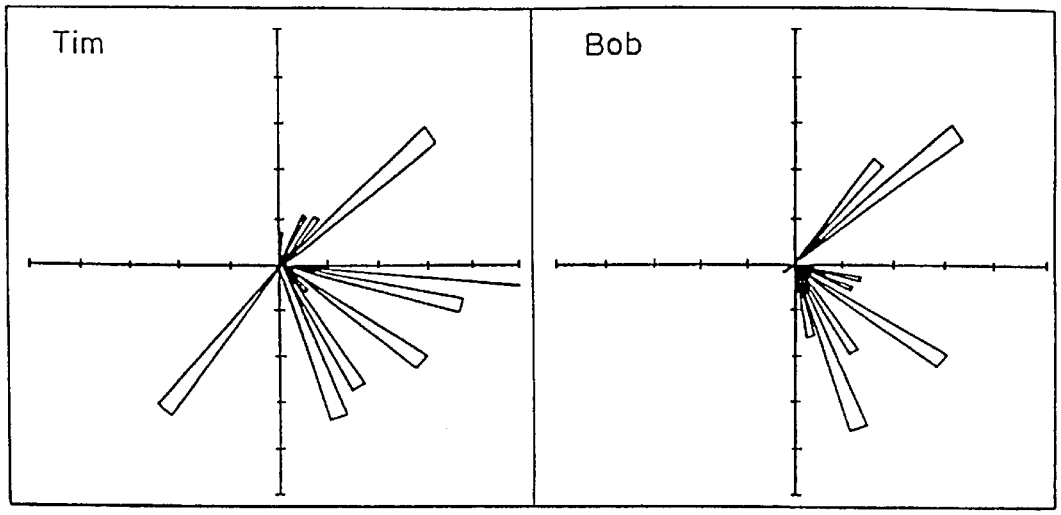
FIG. 9A                FIG. 9B
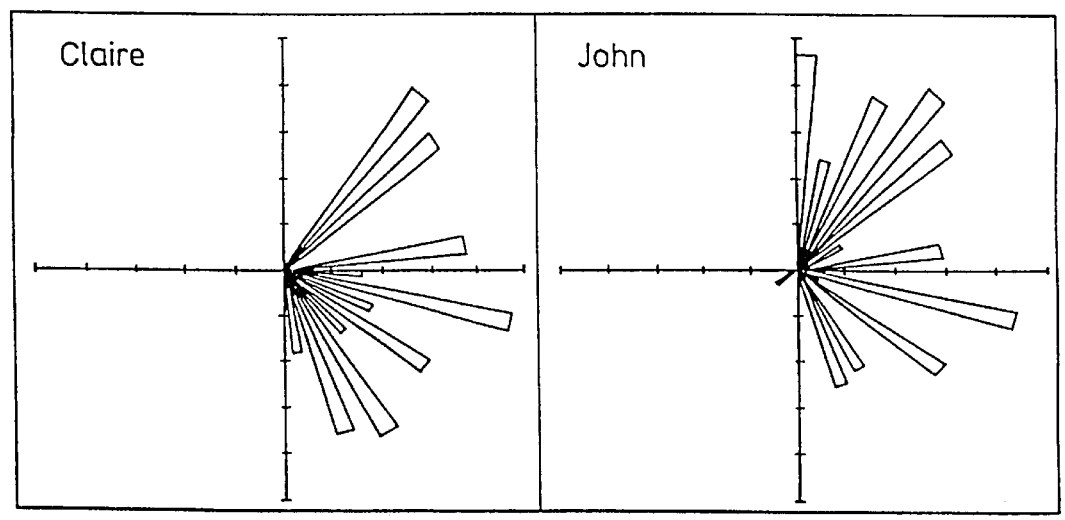
FIG. 9C                FIG. 9D
FIG. 9

ODOR SENSOR

FIELD OF THE INVENTION

This invention relates to an odour sensor particularly but not exclusively for discrimination between the odour of human or other mammalian individuals.

BRIEF DESCRIPTION OF THE DRAWINGS

FIG. 9 shows a comparison between responses of sensors from four individuals.

DESCRIPTION OF THE PREFERRED EMBODIMENTS

Figure 1A:
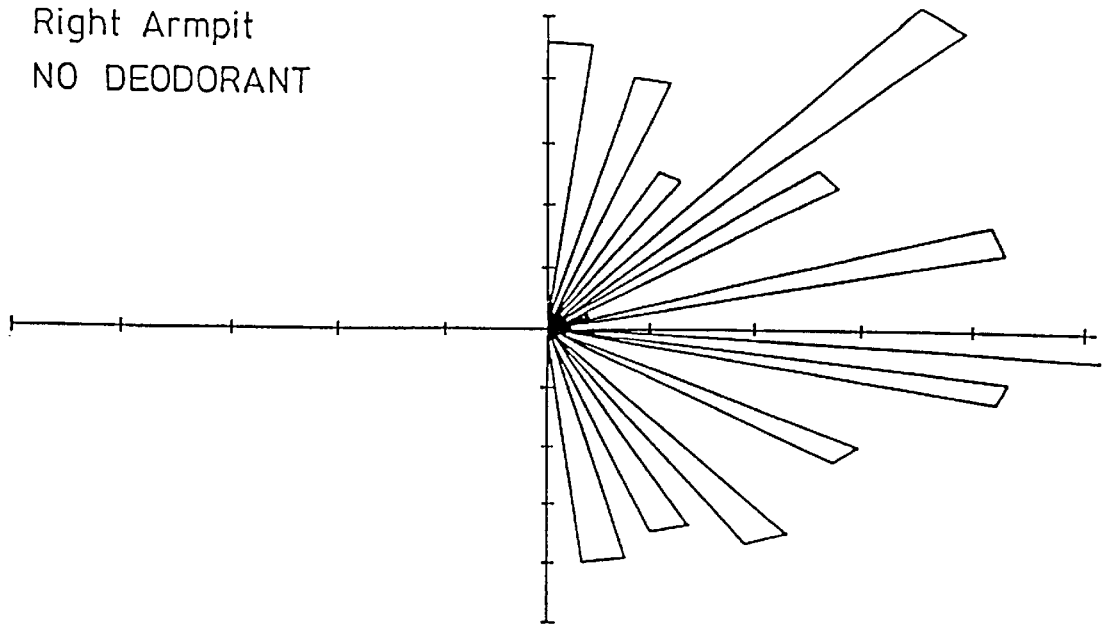
FIG. 1 shows the odour profiles of a human individual with or without deodorant.

Sensors are important for a variety of applications including food freshness, head space analysis of beverages and detection and quantification of bacteria. Sensors have been prepared on interdigitated gold electrodes by polymerising a number of monomers using chemical or electrochemical techniques. The polymers produced are electrically conducting and have varying sensitivities to volatile odour compounds. Interaction of an odour compound with a conducting polymer is detected by a change in the electronic characteristics particularly the resistance, impedance, reactance or capacitance of the polymer film, which may be indirectly measured using changes in the applied potential or current.

According to a first aspect of the present invention a personnel recognition sensor comprises a multiplicity of differentially responding chemo-resistor elements, each element comprising a non-conductive substrate, a plurality of electrodes disposed on the substrate and one or more layers of a conductive polymer overlaying the electrodes, the conductive polymers of at least two of the elements being different;

a detector responsive to signals provided by the multiplicity of elements and arranged to provide an output signal characteristic of the multiplicity of signals;

the elements being disposed in a housing having an inlet arranged so that a gaseous sample passing into or through the inlet contacts all of the elements in use.

A personnel recognition sensor in accordance with this invention is adapted to discriminate between human individuals (or individuals of other mammalian species).

A preferred sensor may incorporate display means adapted to provide a display characteristic of the signals from an individual. Such a display may be referred to as an odour profile.

In a preferred aspect of the present invention the personnel recognition sensor is adapted to identify a human individual.

The sensor may further include a memory adapted to store a library of odour profiles characteristic of particular individuals and means for comparison of the odour profile constituted by the multiplicity of signals from the sensor elements with an odour profile contained in said library. Standard pattern recognition techniques or a neural network may be adapted to retain characteristic features of the multiplicity of signals for incorporation into the library.

The sensor may further comprise a sample collector. The sample collector may comprise means for drawing a predetermined volume or amount of ambient atmosphere from the vicinity of an individual. The collector may define an enclosed or partially enclosed chamber into which an individual or a part thereof may be disposed. A compartment in which a user's hand may be inserted may form a convenient collector. The collector may further include means for drawing air from the vicinity of the user's hand into the sensor closing. Gas may be circulated repeatedly within the collector and/or housing to enhance the concentration of odour analytes.

An unexpected property of sensors in accordance with the present invention is that characteristic odour profiles may be obtained in the presence of odiferous cosmetic compositions including perfumes and deodorants. The sensors have no significant response to the common odour volatiles present in cosmetics but are very responsive to human body odour volatiles. This facilitates use of the sensor for identification of an individual in day to day situations.

A wide range of conductive polymers may be employed.

Conductive polymers may be selected from the group comprising the following substituted derivatives: perimidine, polybenzene, polyphenylenesulphide, polyacetylene, polyaniline, polyphenylenediamine, polypyrrole, polythiophene, polyindole, polyimidazole, polythiazole, polybithiophene, polyphthalocyanine, polytryptophan and copolymers thereof.

A wide range of dopants may be employed, for example ionic dopants including: nitrate, perchlorate, chloride, bromide, fluoride, sulphate, dodecyl and other alkyl sulphates, sulphonate, alkyl sulphonate, aryl sulphonate, fluoroborate, borate, phosphate, carbonate, iodide, ferricyanide; ferrocyanide, alkyl carboxylic acids (octanoic acid, acetic acid, etc), chromate, thiosulphate, sulphite, silicates and vanadate.

According to a second aspect of the present invention an odour sensor comprises a multiplicity of differentially corresponding chemoresistor elements, each element comprising a non-conductive substrate;

a plurality of electrodes disposed on the substrate and one or more layers of a conductive polymer overlaying the electrodes, the conductive polymers of at least two of the elements being different;

a detector responsive to signals provided by the multiplicity of elements and arranged to provide an output signal characteristic of the multiplicity of signals, the elements being disposed in a housing having an inlet arranged so that a gaseous sample passing into or through the inlet contacts all of the elements in use. Wherein at least one of said conductive polymer is a homopolymer of a monomer of Formula I

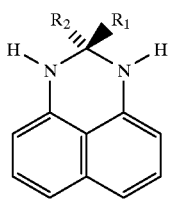

I wherein $R_1$ and $R_2$ are independently: alkyl, alkenyl or alkynyl, aryl, alkylphenyl, alkoxyalkyl, alkylthioalkyl, carboxyalkyl, alkylcarboxyalkyl, arylcarboxyalkyl, naphthyl, ferrocenyl, an alicyclic group or a heterocyclic group; optionally substituted with one or more halogen, hydroxyl, carboxyl, amino, nitrile, thiol, trimethylsilyl, nitro or epoxy groups.

It is preferred that at least one of $R_1$ and $R_2$ is a group having more than 6 carbon atoms.

Substituted perimidine derivatives of Formula I have the advantage that the substituents $R_1$ and $R_2$ do not lie in the plane of the polymer chain. A wide variety of substituents may be employed. The substituents may be selected to enhance the interaction with specific analytes. Examples of substituents $R_1$ and $R_2$ include biologically active molecules and other compounds including: crown ethers, chelates, polyalkylene oxides such as polyethylene glycols, steroids, lipids, boranes, phthalocyanines, crystal violet or thionine or other dyes, saccharides such as lactitol, sorbitol or mannitol, amino acids such as methionine, tyrosine, tryptophan or phenylalanine, nucleic acids such as cytosine, guanine or adenine, antibiotics such as actinomycin D, tetrathiofulvalene, prostoglandin, permidine, spermine, anionic or cationic polyelectrolytes such as dextran sulphate, diethylamino ethyldextran or Gafquat (Trade Mark), haeme derivatives.

In preferred polymers $R_1$ is methyl. $R_2$ is independently preferably methyl, 4-biphenyl, 4-butyric ethyl ester, 3-hydroxyphenyl, ferrocenyl or 3-aminophenyl. The sensor according to the second aspect may be used for personnel recognition food analysis and quality control identification of bacterial infection, prediction of oestrus in livestock and environmental monitoring.

The invention is further described by means of example but not in any limitative sense, with reference to the accompanying drawings.

Preferred chemo-resistor elements have electrodes arranged in an interdigitated array. The electrodes may be fabricated by deposition of gold or other conductive metal onto an insulating substrate such as alumina, glass, silicon or other materials known to those skilled in the art.

A first preferred element comprises laminar alumina substrate having an active surface area of 35 mm² with 30 μm gaps between the interdigitations. A second preferred arrangement uses a silicon substrate with an active surface area of 4–6 mm² with gaps of 30 μm or 4 μm between the interdigitations depending on the polymer employed.

Preferred arrangements incorporate rectangular interdigitations. In preferred arrangements the ratio of the width between the interdigitations and the length of the interdigitations is between 1:20 and 1:1000 most preferred 1:60 and 1:500. The overall area of the transducer surface preferably remains constant when the gap size is changed to alter the ratio. In a preferred embodiment the overall surface area of the interdigitated structures remains constant at 6 mm² with a ringer length of 1.8 mm. With a gap size of 30 μm the ratio of gap size to finger length is 1:60 (30 μm:1800 μm). With a gap size of 4 μm the ratio is 1:450 (4 μm:1800 μm).

The metal surfaces of the transducers may be cleaned using chromic acid and washed well with double distilled water. If electrochemical polymerisation is employed, the gold surfaces may be pre-treated by cycling in an electrochemical cell usually between maximum voltages of to −0.1 v to 2.0 v in the polymerisation buffer to produce an electrochemically clean surface. Specific voltages may be chosen as appropriate.

Chemical polymerisation may be carried out using suitable oxidising agents such as sodium persulphate, sodium periodate, ferric nitrate, ferric perchlorate and the like added to a solution of the monomer deposited onto the upper surface of the cleared transducer. The solution may be acidic, basic or neutral and usually having a concentration between 0.1M and 4.0M, most commonly between 0.5M and 1.0M. The polymeric material is formed as an insoluble layer and the upper surface of the interdigitated area covers the whole active surface of the transducer.

Electrochemical polymerisation may be achieved by incorporating the interdigitated transducer into an electrochemical circuit as the anode or cathode dependent on the polymer species to be formed. Anodic deposition, the most common technique, is carried out by immersion of the transducer in a monomer solution with a platinum counter-electrode adjacent the surface and a reference electrode (silver/silver chloride or calomel) connected into the circuit via a salt bridge. The salt bridge avoids contamination of the reference electrode. The system may then be either maintained at constant potential or alternatively the potential may be cycled between two predetermined values to allow formation of the polymer film on the transducer surface. The detailed conditions vary from monomer to monomer as described below. After polymerisation the sensor is washed and dried either in an oven or using a desiccator.

Perimidine derivatives in accordance with this invention are synthesised as follows.
2,2-Dimethylperimidine
Synthetic route:

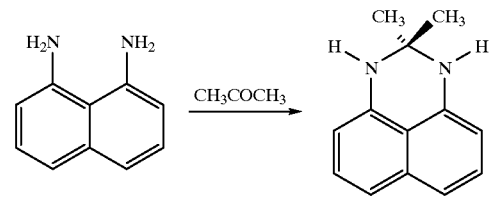

Synthetic procedure:

Diaminonaphthalene 10 g and p-toluenesulphonic acid monohydrate 0.15 g were dissolved in ethanol 20 cm³ and acetone 4 g. The solution was maintained at 60° C. for 2 hours and was then stored overnight in a refrigerator. The product was filtered and washed with ethanol. Crude yield was 73.3% and the material was recrystallised from ethanol to obtain a pure product.

Polymerisation procedure:

| | | |
|---|---|---|
| Monomer concentration | 1 mg/cm³ | |
| Counter-ion (tetrabutylammonium perchlorate) concentration | 0.01M | Use 3 volumes solution to 2 volumes of counter-ion |

| | |
|---|---|
| Solvent | Acrylonitrile |
| Potential | Cyclic between 0.0 and 0.75 V |
| Growth time | 12 min |

2-Methyl-2-(4-biphenyl)perimidine
Synthetic route:

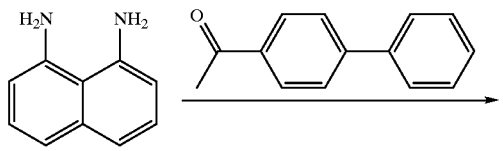

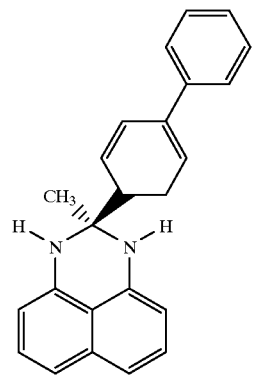

Synthetic procedure:

Diaminonaphthalene 6.32 g, p-toluenesulphonic acid monohydrate 0.07 g and 4-acetyl biphenyl 8.4 g were dissolved in ethanol 40 cm³. The solution was maintained at 50° C. for 6 hours and was then stored overnight in a refrigerator. The product was filtered, washed with ethanol and dried at 50° C. The crude yield was 76.5% and the product was further recrystallised from ethanol to obtain pure 2-methyl-2-(4-biphenyl)perimidine.

Polymerisation procedure:

| | |
|---|---|
| Monomer concentration | 0.1M |
| Counter-ion (tetrabutylammonium perchlorate) concentration | 0.1M |
| Solvent | Acrylonitrile |
| Potential | 0.9 V |
| Growth time | 10 min |

2-Methyl-2-(4-butyric ethyl ester)perimidine
Synthetic route:

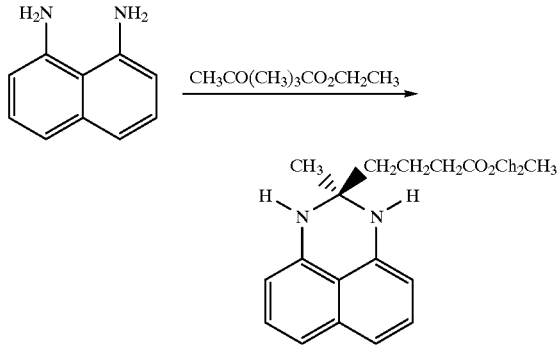

Synthetic procedure:

Diaminonaphthalene 17.98 g, p-toluenesulphonic acid monohydrate 0.3 g and ethyl 4-acetyl butyrate 19.82 g were dissolved in ethanol 100 cm³. The solution was maintained at 50° C. for 6 hours under nitrogen and was then stored overnight in a refrigerator. The product was filtered, washed with ethanol and dried at room temperature. The crude yield was 96.65%. The product was purified by elusion through a silica column with methylene chloride to obtain very pure product.

Polymerisation procedure:

| | |
|---|---|
| Monomer concentration | 0.1M |
| Counter-ion (tetrabutylammonium perchlorate) concentration | 0.1M |
| Solvent | Acrylonitrile |
| Potential | 1.0 V |
| Growth time | 10 min |

2-Methyl-2-(3-hydroxylphenyl)perimidine
Synthetic route:

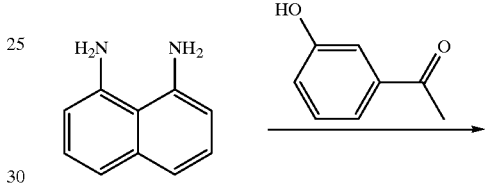

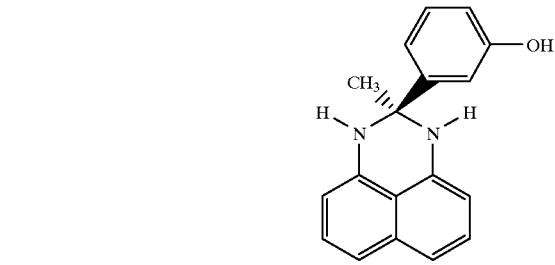

Synthetic procedure:

Diaminonaphthalene 12.64 g, p-toluenesulphonic acid monohydrate 0.02 g and 3-acetylphenol 10.88 g were dissolved in toluene 120 cm³. After refluxing for 2 hours the solution was cooled, filtered, washed with toluene and dried at 50° C. The crude yield was 69.7% and the product was further recrystallised 3 times from toluene to obtain pure 2-methyl-2-(3-hydroxyphenyl)perimidine.

2-Methyl-2-ferrocenylperimidine

Synthetic route:

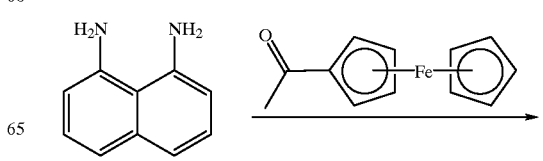

-continued

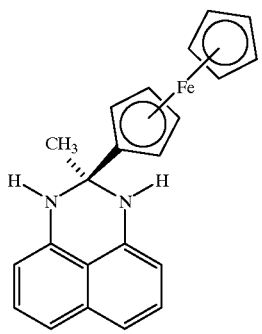

Synthetic procedure:
Diaminonaphthalene 1.58 g, p-toluenesulphonic acid monohydrate 0.08 g and acetylferrocene 2.28 g were dissolved in toluene 30 cm$^3$ and refluxed for 4 hours. The solution was cooled, filtered, washed with toluene and dried at 50° C. The crude yield was 69.7% and the product was recrystallised from toluene to obtain pure 2-methyl-2-ferrocenylperimidine.

2-Methyl-2-(3-aminophenyl)perimidine
Synthetic route:

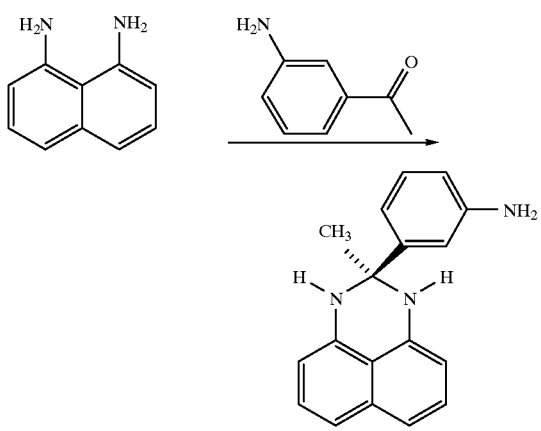

Synthetic structure:
Diaminonaphthalene 1.58 g, p-toluenesulphonic acid monohydrate 0.1 g and 3-acetylaniline were dissolved in toluene 30 cm$^3$ and refluxed for 2 hours. The solution was cooled to 0° C., filtered, washed with toluene and dried at 50° C. The crude yield was 60% and the product was recrystallised from toluene to obtain pure 2-methyl-2(3-aminophenyl)perimidine.

The following Examples illustrate polymerisation processes.

Poly-1,4-phenylenediamine
A solution of 1,4-phenylenediamine hydrochloride (100 mg·ml$^{-1}$) was diluted in 0.1M KCl solution (100 μl into 40 ml KCl solution). The transducer was incorporated as the anode in the circuit and the potential was held constant at +0.5 v for 30 min to produce the polymer, which was washed and dried in air overnight then over silica gel.

Polyimidazole
A solution of imidazole (0.05M) was prepared in 1M KCl. The transducer surface was first precycled 6 times in 1M sulphuric acid between −0.1 v to +1.8 v at a rate of 50 mv.sec$^{-1}$ and then 6 times in 1M KCl between 0.0 v to 1.2 v at the same scan rate. The clean pretreated transducer was then placed into the imidazole solution and the voltage stepped up in +0.1 v increments after each cycle up to +1.4 v when the voltage was held constant for a further 5 min. The sensor was then cleaned and dried as before.

Polyquinoline
A solution of quinoline (0.05M) in 0.1M sulphuric acid was prepared. The transducer was pretreated by cycling 10 times in 0.1M sulphuric acid between 0.0 v to +1.5 v and then immersed in the quinoline solution and cycled between 0.0 v to +0.8 v for 30 min at a scan rate of 50 mv.sec$^{-1}$. The sensor formed was washed and dried as before.

Poly-N-phenyl-1,4-phenylenediamine
A solution of N-phenyl-1,4-phenylenediamine (100 mg·ml$^{-1}$) was prepared in 0.1M HCl and 20 μl was pipetted onto the clean gold surface of a transducer. A solution of ferric perchlorate (40 μl) was added to the monomer solution and the polymerisation allowed to proceed for 10 to 15 min when the surface was washed with distilled water and dried in a 100° C. oven for 2 hours.

Co-polymer of pyrrole and 1-methylpyrrole
A solution of pyrrole (70 mM) and 1-methylpyrrole (30 mM) was prepared in 0.1M KNO$_3$. The transducer was pretreated by cycling 10 times in 0.2 sulphuric acid between −0.1 v to +0.8 v and then 10 times in 0.1M KNO$_3$ between −0.1 v to +0.8 v at a scan rate of 50 mv.sec$^{-1}$. The polymer was formed by holding at a constant potential of +0.65 v for 60 min and the sensor formed was washed and dried in air as before.

Polymers prepared using similar techniques include: polypyrroles, polythiophenes, polyindoles, polyphthalocyanines, polyanilines, polycarbazoles, polythionine, polyaminonaphthalenes, polyaminoanthracenes, polyphenylenediamines, polyaminiophenols, polynaphthyl(ethylenediamine), polyimidazoles, polyquinolines, polytryptophan, polyhetero cycles, polyaminohetero cycles and substituted derivatives of the above compounds. Also copolymers and blends of the above compounds may be employed. The listed polymers may be treated with various ionic dopant molecules incorporated into the conducting films during and post polymerisation. Such ions include: nitrate, perchlorate, chloride, bromide, fluoride, sulphate, dodecyl and other alkyl sulphates, sulphonate, alkyl sulphonate, aryl sulphonate, fluoroborate, borate, phosphate, carbonate, iodide, ferricyanide, ferrocyanide, alkyl carboxylic acids (octanoic acid, acetic acid, etc), chromate, thiosulphate, sulphite, silicates and vanadate.

Acidic proteins and enzymes may be incorporated into partially charged conductive films during or post polymerisation. The selectivity of the sensor may thereby be modified using biological molecules to give sensitivity to specific molecules.

The sensors produced may be incorporated into a multiple array and may comprise between 3 to several hundred sensors. Multiple arrays may incorporate 16 and 32 sensors and may be arranged to operate from either a constant current or constant voltage power supply. The sensor array may be disposed in the housing adapted to allow flow of a gaseous sample over each of the sensor elements. A gaseous sample may be simply injected into the space above the array. Alternatively a piston, bellows or other pump arrangement may be employed.

A sample collector may comprise an enclosed or partially enclosed chamber through which a person's hand or other body part may be inserted. Air drawn from the chamber is circulated over the sensor array and the change in resistances of the elements is detected and quantified using a data acquisition board interfaced directly with a microprocessor.

The odour profile obtained may be represented in any convenient manner, for example a 2D or 3D chart, a 360° polar chart or simply as tabulated data.

The sample of odour volatiles may be introduced into the sensor array using a pump to deliver a metered dose of sample. Alternatively the introduction of the surface of a human hand in close proximity to the sensor array surface has been found to be sufficient to elicit a distinctive response and produce odour profiles which discriminate between human subjects. To this end a sensor array has been mounted under a grille which has the function of physically separating the skin surface from the sensor array at a defined distance (between 2 and 10 mm, most frequently 4 mm) and allowing a sample of skin odour volatiles to impinge on the upper surface of the sensors to elicit the sensor response. Withdrawal of the hand surface from the grille allows the sensor array to re-establish the baseline response seen before the hand was placed in proximity to the sensors.

Figure 1B:
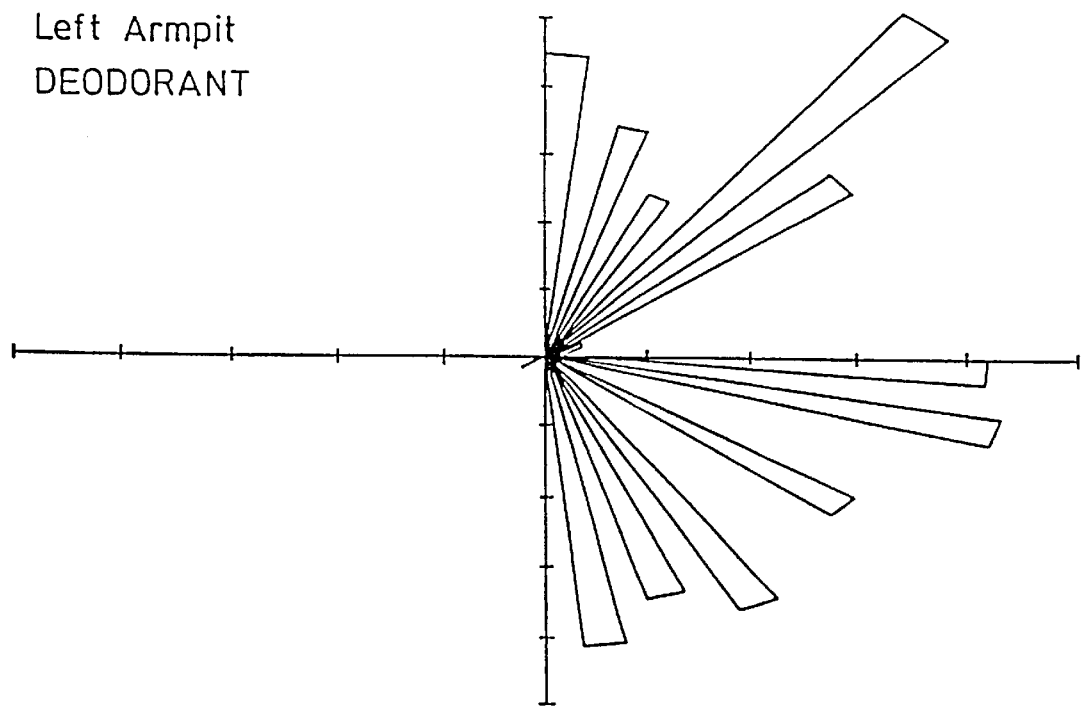

FIG. 1 shows the response of a 16 sensor array to the odour produced from a subject collected in a syringe and blown across the array. Samples taken from the subject's armpits, one of which has been treated with a deodorant are injected into the sensor. The sensor elements comprise the following polymers:

| | Polymer | Dopant |
|---|---|---|
| 1) | Poly-n-ethylaniline | $SO_4$ counter ion |
| 2 and 3) | Poly-aniline | $SO_4$ counter ion |
| 4 and 5) | Poly-tryptophan | $SO_4$ counter ion |
| 6) | Poly-2-methoxy-5-nitroaniline | $SO_4$ counter ion |
| 7) | Thiophene/thiophene-3-carboxylic acid copolymer | Tetrabutyl-ammonium perchlorate counter ion |
| 8) | Poly-aniline with ethanol | $SO_4$ counter ion |
| 9) | Poly-pyrrole | Octanoic acid ethyl ester dopant |
| 10) | Poly-pyrrole with upper layer of poly-tryptophan | Octanoic acid ethyl ester dopant $CO_4$ counter ion |
| 11 and 12) | Poly-1,4-phenlene diamine | Cl counter ion |
| 13) | Poly-pyrrole | Cl counter ion |
| 14) | Poly-pyrrole | Tetrabutyl-ammonium perchlorate counter ion |
| 15) | Pyrrole/1-methyl pyrrole copolymer | $NO_3$ counter ion |
| 16) | Poly-pyrrole | Octanoic acid ethyl ester dopant |

The two profiles are essentially the same indicating that the odour sensor does not respond to the deodorant but responds to the body odour of the individual.

Figure 2A:
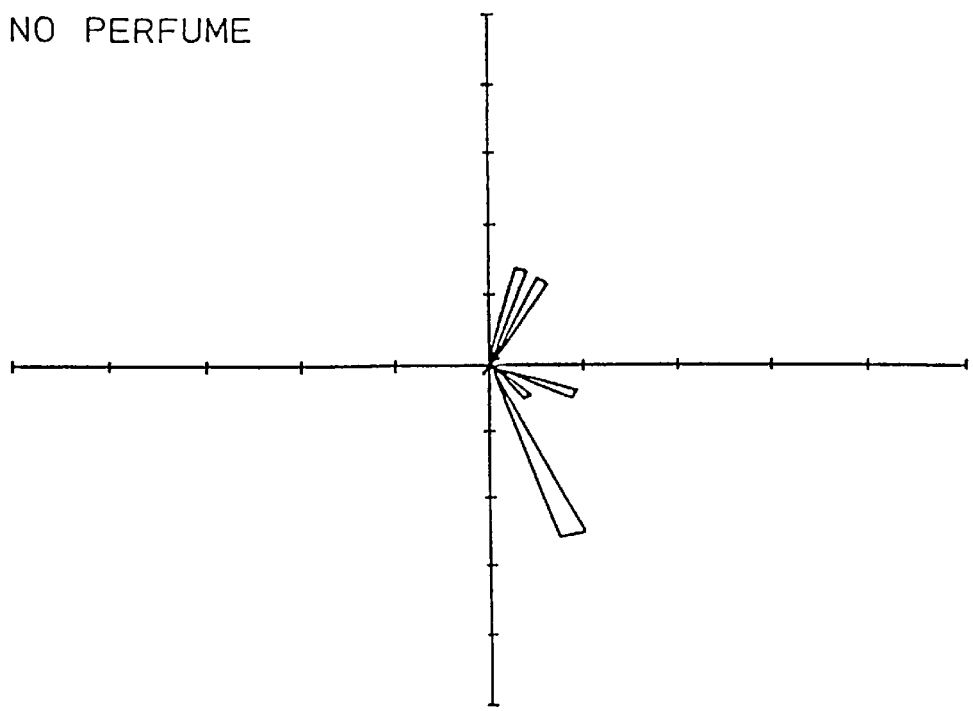
FIG. 2 shows odour profiles of a human with or without perfume.
Figure 2B:
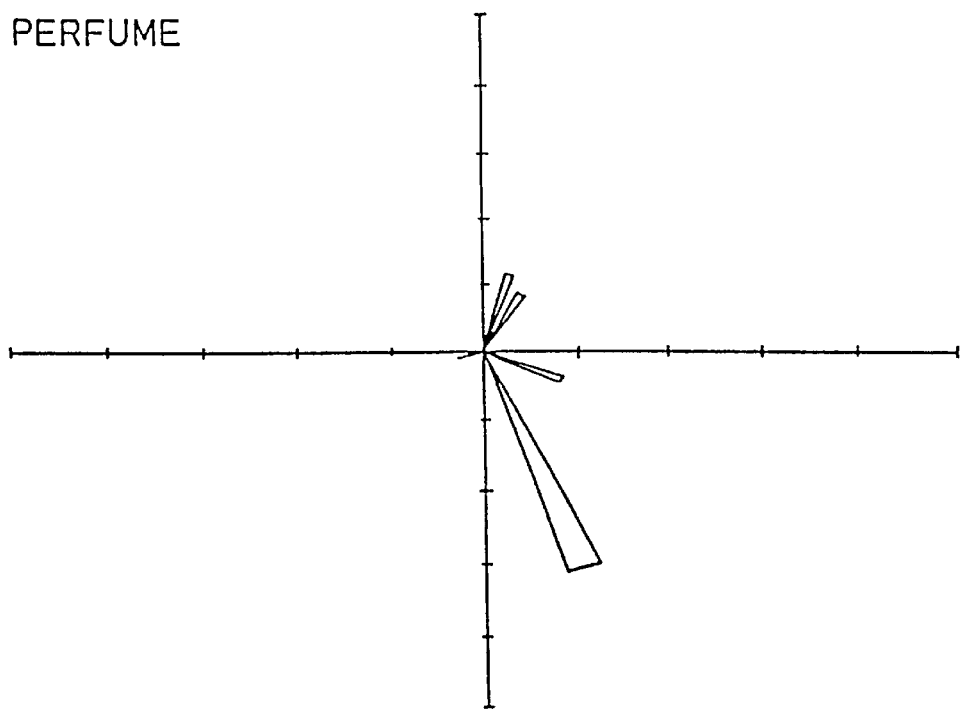

FIG. 2 shows the odour profile of a human hand which has been sampled by the 16 sensor array as in FIG. 1, located under a grille as described above. One hand is treated with neat perfume and the other has not been treated. The profiles are virtually identical indicating that the sensor responses are due to body odour and not to the chemical components of the perfume.

Figure 3:
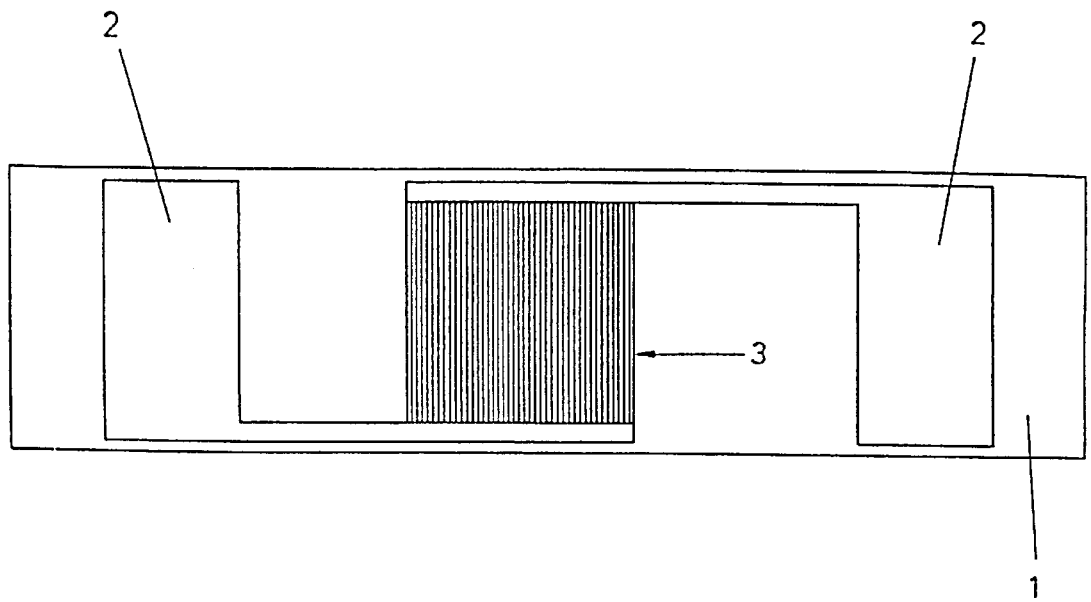
FIG. 3 is a plan view of a sensor element in accordance with the invention.

FIG. 3 is a plan view of a sensor element in accordance with this invention. A laminar alumina substrate 1 carries gold electrode layers 2 forming an interdigitated transducer 3. The interdigitated transducer has an area of 35 $mm^2$ with gaps of 30 $\mu m$ between the interdigitations. The sensor array is produced by placing 16 completed sensors (transducers with the deposited polymers) into a custom built moulding that allows flow through of airborne samples or sampling directly from the skin.

Figure 4:
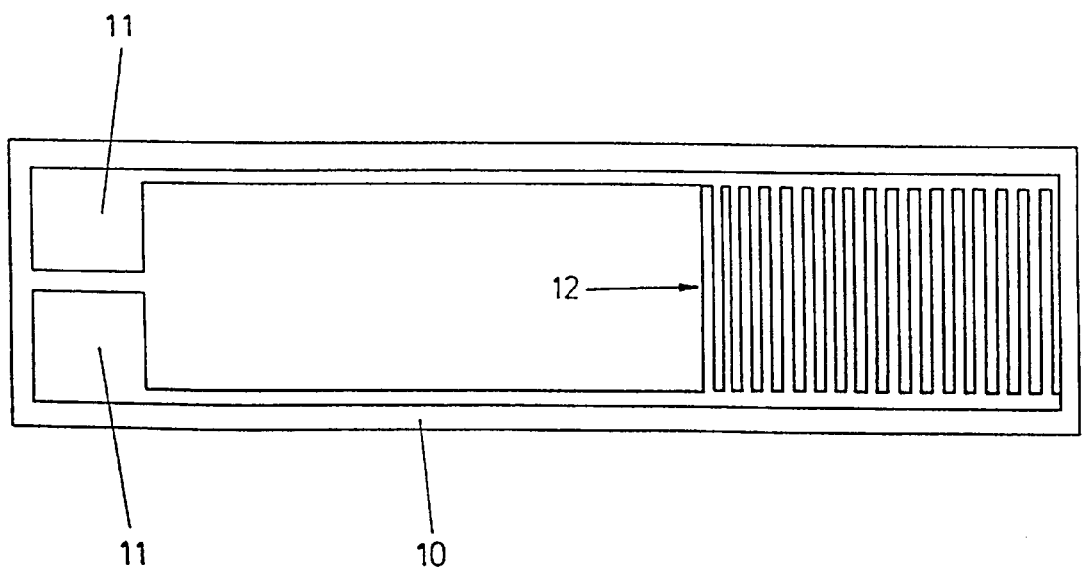
FIG. 4 is a plan view of an alternative sensor in accordance with the invention.

FIG. 4 illustrates an alternative configuration wherein a silicon substrate 10 supports gold electrodes 11 forming an interdigitated transducer 12. The area of the transducer is 6 $mm^2$ with gaps of 30 $\mu m$ or 4 $\mu m$ for type 1 and 2 respectively. Polymers having inherently high baseline resistances eg polytryptophan, polyimidazole are deposited on the transducers having narrower gaps.

Figure 5:
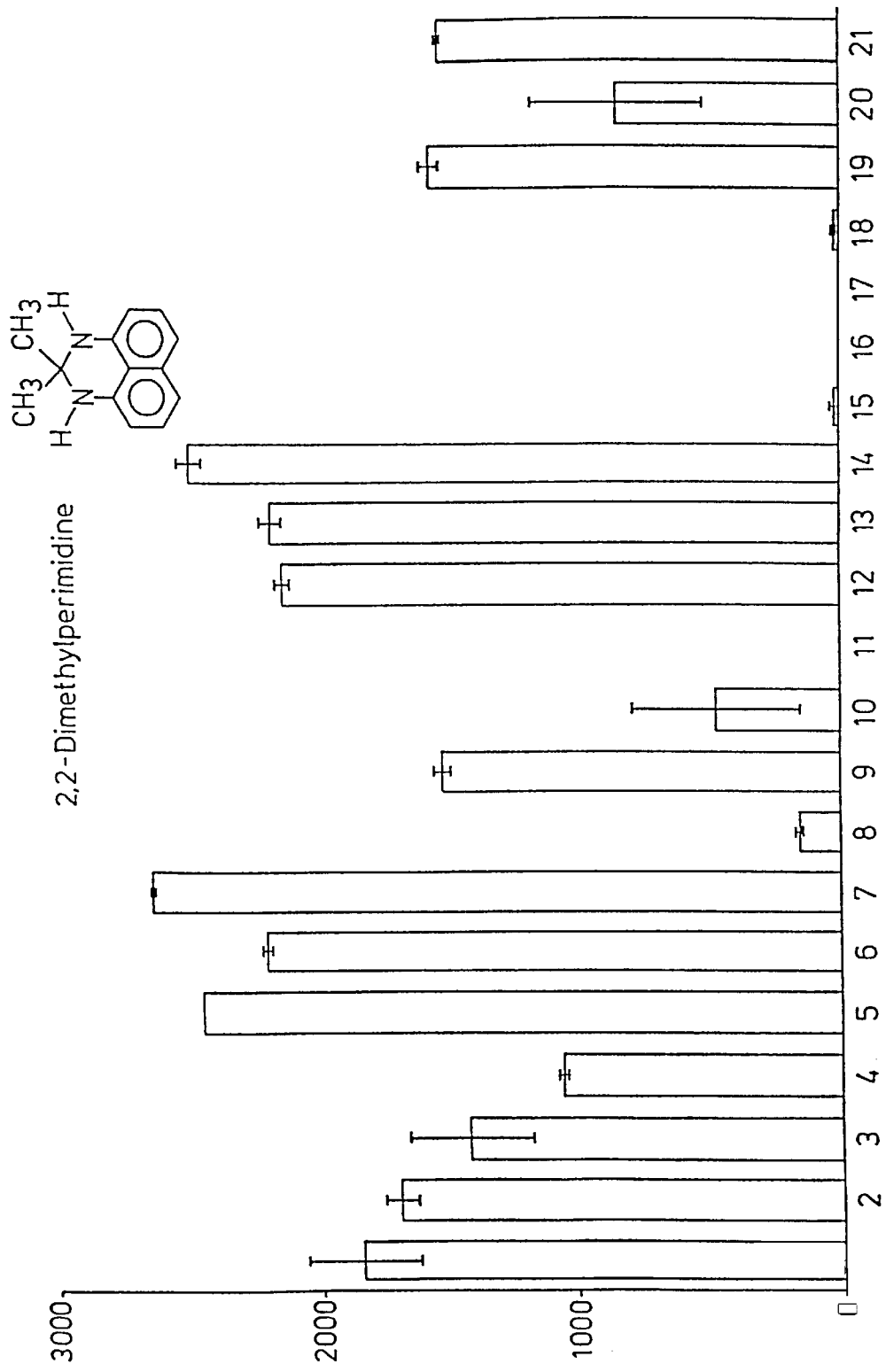
FIGS. 5, 6, 7 and 8 show responses of sensors comprising substituted perimidines.
Figure 6:
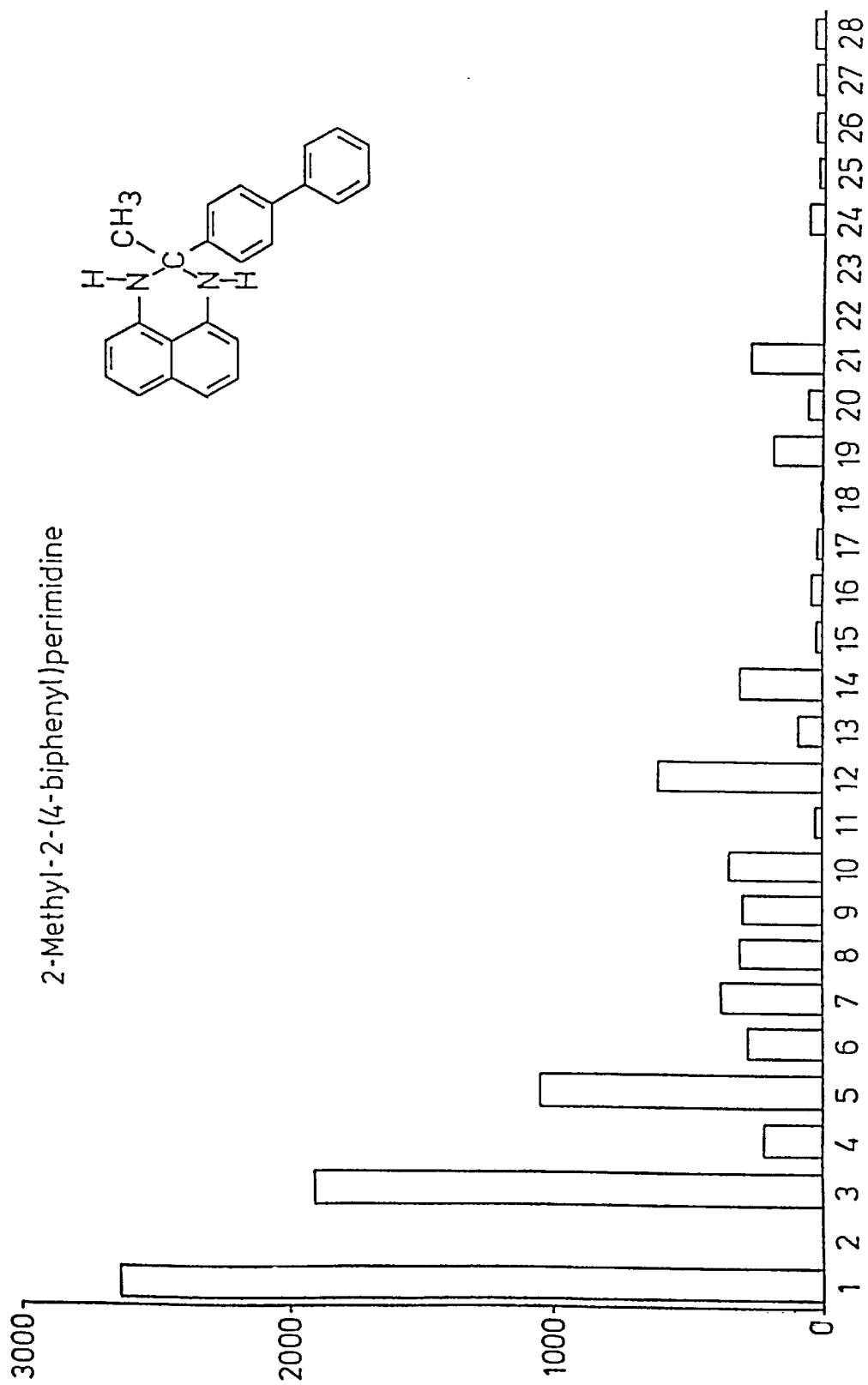
Figure 7:
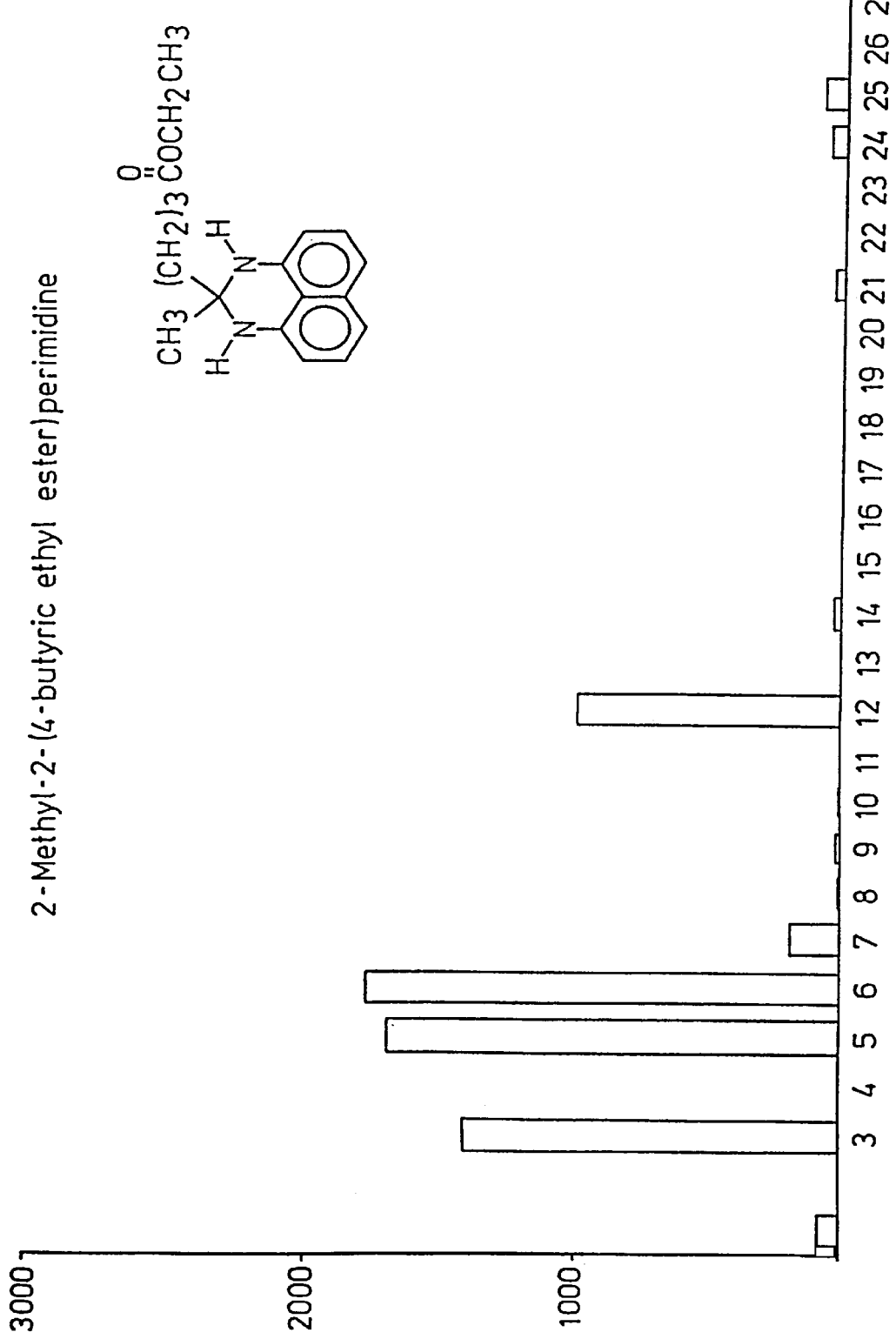

FIGS. 5 to 7 illustrate the response of sensor elements in accordance with this invention to gaseous specimens containing compounds representative of those found in human odour.

FIG. 5 illustrates the characteristic of a sensor elements comprising 2,2-dimethylperimidine, FIG. 6 illustrates the characteristic of a sensor element comprising 2-methyl-2-(4-biphenyl)perimidine and FIG. 7 illustrates the characteristic of a sensor element comprising 2-methyl-2-(4-butyric ethyl ester)perimidine. These Figures show the relative magnitude of changes in each element when the sensor is exposed to the vapour of the chemicals listed below. Each column is the mean of five measurements and error bars where shown are at +/−1 standard deviation from the mean.

A 5 $cm^3$ aliquot of the liquid under test was placed in a 50 ml glass bottle fitted with a gas head, three way taps and a syringe for use when dilution of the sample was necessary. The bottle was suspended in a water bath at 40° C. until the headspace became saturated with the volatile. An aliquot of the headspace was then passed over sensors using the pump and solenoid valve system. This system comprised a variable speed electrically powered gas pump and a solenoid valve set to switch from filtered air to the volatile and back again after a set time. The pump speed and the timing of the solenoid were set such that a 20 ml sample of the volatile in air passed through the sensor chamber. This chamber included a carrier holding 16 sensors and incorporating the electrical connections required for resistance measurement. The resistance data acquisition and processing was carried out by a personal computer using dedicated software.

The response of the sensor elements in relation to the compounds listed in the key below is shown in the corresponding numbered columns of the figures.

Figure 8:
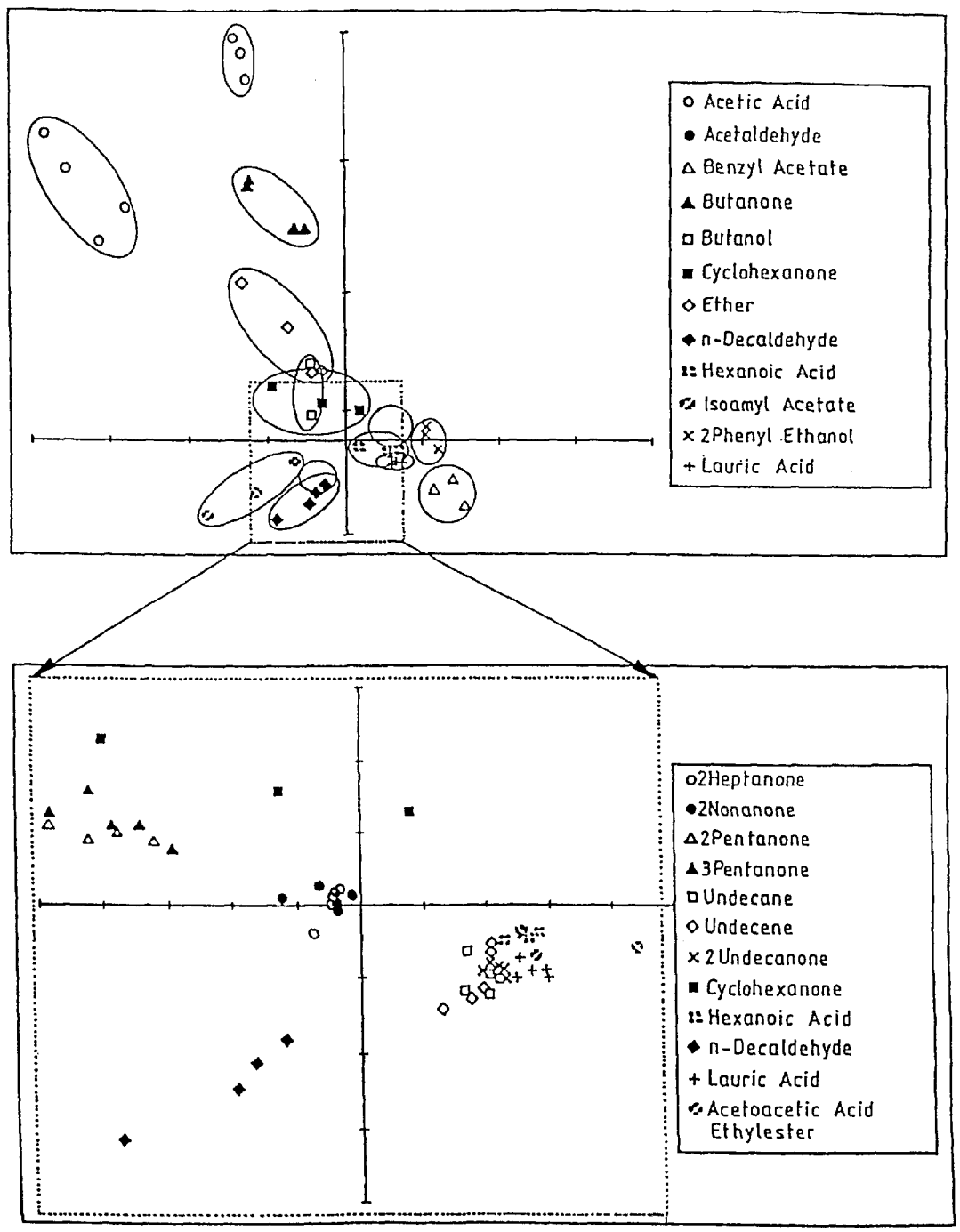

1. Acetic Acid
2. Acetoacetic acid ethylester
3. Acetaldehyde
4. Benzyl Acetate
5. ½ DilutionButylamine
6. Butanone
7. Butanol
8. Cyclohexanone
9. N Decylaldehyde
10. 2,4 Dichlorophenol
11. 1,2 Ethane diolmonobenzoate
12. Ether
13. Hexanoic Acid
14. Isoamyl Acetate
15. Isovaleric acid
16. Lauric Acid
17. 2-Methyl 2-nonanol
18. Phenol
19. 2Phenyl Ethanol
20. Toluene
21. 111Trichloroethane
22. 2-Heptanone
23. 2-Nonanone
24. 2-Pentanone
25. 3-Pentanone
26. Undecane
27. Undecene
28. 2-Undecanone FIG. 8 is a representation of the responses of a sensor comprising 16 elements of which three elements comprise substituted perimidine homopolymers, to specific compounds important for recognition of individuals. Each point is a vector interpretation of the entire response from one sample. Each compound has been sampled four times. The Figure shows consistent differentiation between the compounds. The sensitivity of the array of elements to those compounds enables personnel identification to be facilitated.

FIG. 9 is a comparison between the responses to four individuals obtained using the sensor described with reference to FIG. 1.

The reproducible responses allow positive identification of each individual on subsequent occasions.

We claim:

1. An odour sensor comprising a multiplicity of differentially corresponding chemoresistor elements, each element comprising a non-conductive substrate;

a plurality of electrodes disposed on the substrate and one or more layers of a conductive polymer overlaying the electrodes, the conductive polymers of at least two of the being different;

a detector responsive to signals provided by the multiplicity of elements and arranged to provide an output signal characteristic of the multiplicity of signals, the elements being disposed in a housing having an inlet arranged so that a gaseous sample passing into or through the inlet contact all of the elements in use;

wherein at least one of said conductive polymers is a homopolymer of a monomer of Formula I

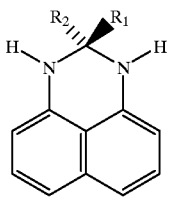

I wherein $R_1$ and $R_2$ are independently: alkyl, alkenyl or alkynyl, aryl, alkylphenyl, alkoxyalkyl, alkylthioalkyl, carboxyalkyl, alkylcarboxyalkyl, arylcarboxyalkyl, naphthyl, ferrocenyl, an alicyclic group, a heterocyclic group; optionally substituted with one or more halogen, hydroxyl, carboxyl, amino, nitrile, thiol, trimethylsilyl, nitro or epoxy groups.

2. A sensor as claimed in claim 1 wherein $R_1$ is methyl.

3. A sensor as claimed in claim 2 wherein $R_2$ is selected from methyl, 4-biphenyl, 4-butyric ethyl ester, 3-hydroxyphenyl, ferrocenyl, 3-aminophenyl.

4. A sensor as claimed in any preceding claim, wherein the electrodes are arranged in an interdigitated array, the ratio between the width of the interdigitations and the length of the interdigitations is 1:20 to 1:1000.

5. A sensor as claimed in claim 4, wherein the ratio is 1:60 to 1:500.

* * * * *